US007922992B2

(12) United States Patent  
Ernst et al.

(10) Patent No.: US 7,922,992 B2
(45) Date of Patent: Apr. 12, 2011

(54) COMPOSITION AND METHOD FOR PRODUCING CARBON DIOXIDE

(75) Inventors: William Ernst, Roswell, GA (US); Joel Tenney, Marietta, GA (US); Tom Isaac, Newnan, GA (US)

(73) Assignee: ICA Trinova, LLC, Forest Park, GA (US)

( * ) Notice: Subject to any disclaimer, the term of this patent is extended or adjusted under 35 U.S.C. 154(b) by 1763 days.

(21) Appl. No.: 10/243,590

(22) Filed: Sep. 13, 2002

(65) Prior Publication Data

US 2004/0051080 A1    Mar. 18, 2004

(51) Int. Cl.
*A23L 3/3427* (2006.01)
(52) U.S. Cl. .............. 423/438; 252/183.11; 252/183.16; 252/186.25; 252/186.36; 426/263
(58) Field of Classification Search .................. 423/438; 426/263; 252/186.25, 186.36, 183.16, 183.11
See application file for complete search history.

(56) References Cited

U.S. PATENT DOCUMENTS

| | | |
|---|---|---|
| 2,163,793 A | 6/1939 | Logan |
| 2,482,891 A | 9/1949 | Aston |
| 2,885,368 A | 5/1959 | Hess et al. |
| 3,049,399 A | 8/1962 | Gamson et al. |
| 3,271,242 A | 9/1966 | McNicholas |
| 3,298,780 A | 1/1967 | Fleck |
| 3,382,033 A | 5/1968 | Kitagawa |
| 3,997,462 A | 12/1976 | Denaeyer et al. |
| 4,247,531 A | 1/1981 | Hicks |
| 4,528,171 A | 7/1985 | Casci et al. |
| 4,547,381 A | 10/1985 | Mason et al. |
| 4,554,261 A | 11/1985 | Gergely et al. |
| 4,581,219 A | 4/1986 | Imada et al. |
| 4,585,482 A | 4/1986 | Tice et al. |
| 4,590,057 A | 5/1986 | Hicks |
| 4,610,882 A | 9/1986 | Laurent et al. |
| 4,689,169 A | 8/1987 | Mason et al. |
| 4,695,296 A | 9/1987 | Christe |
| 4,731,193 A | 3/1988 | Mason et al. |
| 4,815,092 A | 3/1989 | Chartier |
| 4,844,981 A | 7/1989 | Landau |
| 4,871,701 A | 10/1989 | Danner et al. |
| 4,889,654 A | 12/1989 | Mason et al. |
| 5,264,227 A | 11/1993 | Laroche et al. |
| 5,278,112 A | 1/1994 | Klatte |
| 5,302,354 A | 4/1994 | Watvedt et al. |
| 5,346,876 A | 9/1994 | Ichimura et al. |
| 5,360,609 A | 11/1994 | Wellinghoff |
| 5,376,164 A | 12/1994 | Zarchy et al. |
| 5,407,656 A | 4/1995 | Roozdar |
| 5,422,330 A * | 6/1995 | Kaylor .......................... 502/402 |
| 5,458,743 A | 10/1995 | Allen |
| 5,567,405 A | 10/1996 | Klatte et al. |
| 5,573,743 A | 11/1996 | Klatte et al. |
| 5,631,300 A | 5/1997 | Wellinghoff |
| 5,639,295 A | 6/1997 | Wellinghoff et al. |
| 5,668,185 A | 9/1997 | Wellinghoff |
| 5,669,176 A | 9/1997 | Miller |
| 5,705,092 A | 1/1998 | Wellinghoff et al. |
| 5,730,948 A | 3/1998 | Klatte et al. |
| 5,776,850 A | 7/1998 | Klatte et al. |
| 5,853,689 A | 12/1998 | Klatte |
| 5,885,543 A | 3/1999 | Klatte |
| 5,974,810 A | 11/1999 | Speronello |
| 5,989,497 A | 11/1999 | Labonte, Jr. |
| 6,055,766 A | 5/2000 | Nolen et al. |
| 6,077,495 A | 6/2000 | Speronello et al. |
| 6,106,775 A | 8/2000 | Fuller |
| 6,174,508 B1 | 1/2001 | Klatte |
| 6,267,953 B1 | 7/2001 | Bernier et al. |
| 6,294,108 B1 | 9/2001 | Speronello et al. |
| 6,379,643 B1 | 4/2002 | Klatte |
| 6,423,289 B1 | 7/2002 | Klatte |
| 6,458,735 B1 | 10/2002 | Klatte |
| 6,503,419 B2 | 1/2003 | Klatte |
| 6,516,559 B1 | 2/2003 | Simchoni et al. |
| 6,592,919 B1 | 7/2003 | Matthews et al. |
| 6,602,466 B2 | 8/2003 | Hamilton et al. |
| 6,607,696 B1 | 8/2003 | Hamilton et al. |
| 2001/0031298 A1 | 10/2001 | Fuller |

(Continued)

FOREIGN PATENT DOCUMENTS

EP    0132049 A1    1/1985

(Continued)

OTHER PUBLICATIONS

Carlson D A et al.: "Yellowfever mosquitoes. Compounds related to lactic acid that attract females" Journal of Economic Entomology, Entomological Society of America. College Park, Maryland, US, vol. 66, No. 2, 1973, pp. 329-331.

(Continued)

*Primary Examiner* — Stuart Hendrickson
(74) *Attorney, Agent, or Firm* — Alston & Bird LLP

(57) ABSTRACT

The invention is a method and composition for producing carbon dioxide that is based on the reaction or activation of at least one carbon-containing compound with protons. The carbon-containing compound can be in the form of a powder, an impregnated carrier (e.g. zeolite crystals) or an aqueous solution and is preferably selected from the group consisting of carbonates, bicarbonates or sesquicarbonates. The protons are preferably provided by a proton-generating species such as an acid or metal salt. The method and composition can further include a water-retaining substance and/or a chlorine dioxide-producing compound in accordance with the invention.

44 Claims, No Drawings

U.S. PATENT DOCUMENTS

| | | |
|---|---|---|
| 2001/0038805 A1 | 11/2001 | Hamilton et al. |
| 2002/0028191 A1 | 3/2002 | Bernier et al. |
| 2002/0036284 A1 | 3/2002 | Speronello et al. |
| 2002/0122813 A1 | 9/2002 | Healy |
| 2003/0053931 A1 | 3/2003 | Hamilton et al. |
| 2003/0217503 A1 | 11/2003 | Robison |
| 2004/0131736 A1 | 7/2004 | Pan et al. |

FOREIGN PATENT DOCUMENTS

| | | |
|---|---|---|
| EP | 0 423 817 A2 | 4/1991 |
| EP | 0 527 228 A1 | 2/1993 |
| EP | 0 710 621 A1 | 5/1996 |
| JP | 52038028 | 3/1977 |
| JP | 56067521 | 6/1981 |
| JP | 57125683 A2 | 8/1982 |
| JP | 58 140312 A | 8/1983 |
| JP | 58161904 | 9/1983 |
| JP | 60000827 | 1/1985 |
| JP | 61256915 | 11/1986 |
| JP | 01071804 | 3/1989 |
| JP | 02 020270 A | 1/1990 |
| JP | 2198629 | 8/1990 |
| JP | 03000979 A | 1/1991 |
| JP | 3023863 | 1/1991 |
| JP | 6285368 | 10/1994 |
| WO | WO-85/05008 | 11/1985 |
| WO | WO-85/05038 | 11/1985 |
| WO | WO 98/11776 | 3/1998 |
| WO | WO98/38865 | 9/1998 |
| WO | WO 99/26471 | 6/1999 |
| WO | WO 00/11944 | 3/2000 |
| WO | WO 00/21580 | 4/2000 |
| WO | WO 00/27187 A2 | 5/2000 |
| WO | WO 00/65910 | 11/2000 |
| WO | WO 00/69775 | 11/2000 |
| WO | WO 01/30150 A1 | 5/2001 |
| WO | WO 01/32013 A1 | 5/2001 |
| WO | WO 02/15683 A1 | 2/2002 |
| WO | WO 02/069723 A2 | 9/2002 |
| WO | WO 03/051406 A1 | 6/2003 |
| WO | WO 03/051407 A1 | 6/2003 |
| ZA | 8 505 940 A | 3/1986 |

OTHER PUBLICATIONS

International Search Report from PCT/US03/28717 dated Jan. 28, 2004.

International Search Report from PCT/US03/28723 dated Feb. 4, 2004.

Masschelein, *Chlorine Dioxide—Chemistry and Environmental Impact of Oxychlorine Compounds* (1979) (Ann Arbor Science Publishers Inc., Ann Arbor, Michigan), pp. 138-141.

Morita, Yasuo et al., "Manufacture of a Solid Chlorine Dioxide Generating Agent," *Chemical Abstracts*, vol. 100, No. 2, Abstract No. 9463, Jan. 9, 1984.

Gao, et al., "Use of Tailored Zeolites for Removal of Benzene and Toluene From Water," 45th Purdue Industrial Waste Conference Proceedings, 1992, pp. 509-515, Lewis Publishers, Inc., Chelsea, Michigan.

Bowman, et al., "Treatment of Waters Contaminated with BTX and Heavy Metals Using Tailored Zeolites," New Mexico Waste-Management and Education Research Consortium, Technical Completion Report (Project No. WERC-91-41), Mar. 1993, pp. 119-144, U S A.

* cited by examiner

COMPOSITION AND METHOD FOR PRODUCING CARBON DIOXIDE

FIELD OF THE INVENTION

The invention relates to methods for producing carbon dioxide, and to mixtures used in performing such methods. In particular, the invention relates to methods of producing carbon dioxide by activating a carbon-containing compound in the form of a powder or present in a porous carrier such as a zeolite crystal with protons from an acid or other proton-generating species.

BACKGROUND OF THE INVENTION

Carbon dioxide ($CO_2$) is useful for food preservation, laboratory research, mosquito control and other applications. There are industrial methods of releasing $CO_2$ by using dry ice or by burning organic fuels such as propane, butane and the like. These industrial methods, however, are limited in their portability and their predictability or control. Furthermore, these methods often require special equipment and/or special handling. These industrial methods are also limited by the fact they must be operated at either low temperatures (in the case of dry ice) or high temperatures (in the case of burning fuels). Dry ice must also be stored at low temperatures or else it will sublimate to produce carbon dioxide during storage.

There is a need in the art to provide a method for producing carbon dioxide that can be conducted at room temperature and that does not require special equipment, handling or storage. Furthermore, there is a need in the art to provide a method for producing carbon dioxide at a controlled rate even at temperatures below 100° F.

SUMMARY OF THE INVENTION

The present invention provides a method for producing carbon dioxide, including the steps of providing at least one carbon-containing compound preferably selected from the group consisting of carbonates, bicarbonates or sesquicarbonates; and activating the carbon-containing compound with protons, thereby producing carbon dioxide as a result of the reaction of the protons with the carbon-containing compound. The carbon-containing compound can be impregnated in a porous carrier such as zeolite crystals or can be provided as a powder and the carrier or powder can be contacted with the protons to produce carbon dioxide. The carbon-containing compound is preferably selected from the group consisting of sodium carbonate, sodium bicarbonate and sodium sesquicarbonate and is more preferably sodium carbonate, sodium bicarbonate, or a mixture thereof. The release of the carbon dioxide produced by the reaction of the carbon-containing compound and protons can be controlled in accordance with the invention. For example, a permeable barrier can be used to control the rate of release, e.g., by controlling the rate at which an activating fluid passes through said barrier to produce carbon dioxide.

The carbon-containing compound is preferably activated by exposing the carbon-containing compound to a proton-generating species and activating the proton-generating species to produce protons that react with the carbon-containing compound to produce carbon dioxide. A porous carrier such as zeolite crystals can be impregnated with the proton-generating species. The proton-generating species can be an aqueous acid or a metal salt and can be activated by a moisture-containing fluid, i.e., a fluid comprising water. The aqueous acid is preferably sulfuric acid and the metal salt is preferably at least one metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CUSO_4$, $CuCl_2$, $MgSO_4$, sodium acetate and sodium citrate. The carbon-containing compound and the proton-generating species can be provided in a dry, airtight container and the proton-generating species activated by opening the container to expose the proton-generating species to a moisture-containing fluid to produce protons that react with the carbon-containing compound to produce carbon dioxide. The method can include the steps of allowing a fluid to contact the proton-generating species to produce protons and allowing the fluid to contact the at least one carbon-containing compound so that the protons react with the carbon-containing compound to produce carbon dioxide. These steps can occur sequentially or simultaneously in accordance with the invention. The fluid is typically a liquid or gas containing water (e.g. water, an aqueous solution, water vapor or air).

At least one water-retaining substance can be provided with the carbon-containing compound and can be impregnated in a porous carrier or can be present as a powder. Preferred water-retaining substances are selected from the group consisting of calcium chloride, magnesium sulfate, potassium chloride and potassium hydroxide. The water-retaining substance can be provided in an amount sufficient to control the rate of release of the carbon dioxide produced by the reaction of the carbon-containing compound and protons. At least one chloride dioxide-producing compound can also be provided with the carbon-containing compound of the invention so that the method produces both carbon dioxide and chlorine dioxide. Preferred chlorine dioxide-producing compounds can be selected from the group consisting of metal chlorites, metal chlorates, chloric acid and hypochlorous acid.

In one preferred method embodiment, the invention includes the steps of providing first zeolite crystals impregnated with at least one carbon-containing compound selected from the group consisting of carbonates, bicarbonates or sesquicarbonates; providing second zeolite crystals impregnated with a proton-generating species; activating the proton-generating species to produce protons; and reacting the protons and the at least one carbon-containing compound to produce carbon dioxide. In accordance with this embodiment, a water-retaining substance can also be provided. Third zeolite crystals impregnated with at least one chloride dioxide-producing compound can also be provided and can react with the protons to produce chlorine dioxide.

In another preferred method embodiment, the invention includes the steps of providing a powder comprising at least one carbon-containing compound selected from the group consisting of carbonates, bicarbonates or sesquicarbonates; providing zeolite crystals impregnated with a proton-generating species; activating the proton-generating species to produce protons; and reacting the protons and the at least one carbon-containing compound to produce carbon dioxide. A water-retaining substance can also be provided. In addition, at least one chloride dioxide-producing compound can be provided and can react with protons to produce chlorine dioxide.

In yet another preferred embodiment, the invention includes the steps of allowing a fluid to contact zeolite crystals impregnated with at least one proton-generating species to produce protons; and allowing the fluid to contact at least one carbon-containing compound selected from the group consisting of carbonates, bicarbonates or sesquicarbonates, wherein carbon dioxide is produced as a result of reaction of the at least one carbon-containing compound and the protons.

These steps can occur sequentially or simultaneously in accordance with the invention. The fluid can contact zeolite crystals impregnated with the carbon-containing compound or a powder comprising the carbon-containing compound. In one particularly preferred embodiment, the fluid contacts zeolite crystals impregnated with sodium bicarbonate as the carbon-containing compound and a water-retaining substance such as calcium chloride. The fluid is typically a liquid or gaseous fluid containing water (e.g. water, an aqueous solution, water vapor or air). In addition to contacting the carbon-containing compound, the fluid can contact a chloride dioxide-producing compound such that carbon dioxide is produced as a result of reaction of the at least one carbon-containing compound and the protons and chlorine dioxide is produced as a result of reaction of the at least one chloride dioxide-producing compound and the protons.

The present invention also includes compositions of matter for the production of carbon dioxide using a carbon-containing compound. In one preferred embodiment of the invention, the composition comprises a plurality of zeolite crystals, at least a portion of the zeolite crystals comprising at least one carbon-containing compound impregnated therein selected from the group consisting of carbonates, bicarbonates or sesquicarbonates. The at least one carbon-containing compound is preferably selected from the group consisting of sodium carbonate, sodium bicarbonate and sodium sesquicarbonate. At least a portion of the zeolite crystals preferably include 1-50% of the at least one carbon-containing compound by weight, 0%-20% water by weight, and 50%-98.5% of the zeolite crystals by weight. The composition preferably further includes at least one water-retaining substance preferably selected from the group consisting of calcium chloride, magnesium sulfate, potassium chloride and potassium hydroxide and at least a portion of the zeolite crystals can be impregnated with the water-retaining substance. The water-retaining substance can be present in an amount that limits the rate of release of the carbon dioxide produced by the composition. The composition also preferably includes a proton-generating species and at least a portion of the zeolite crystals can be impregnated with the proton-generating species. Furthermore, the composition can include at least one chloride dioxide-producing compound preferably selected from the group consisting of metal chlorites, metal chlorates, chloric acid and hypochlorous acid and at least a portion of the zeolite crystals can be impregnated with the chlorine dioxide-producing compound. Preferably, the composition is included in a container and the container can include a carbon dioxide-permeable barrier to allow the passage of carbon dioxide produced in the container, e.g., by exposing the contents of the container to a moisture-containing fluid. The permeable barrier can also be capable of controlling the release of carbon dioxide from the container.

In an alternative embodiment of the invention, the composition includes first zeolite crystals impregnated with at least one carbon-containing compound selected from the group consisting of carbonates, bicarbonates or sesquicarbonates; and second zeolite crystals impregnated with at least one compound selected from the group consisting of a proton-generating species and a water-retaining substance. Preferably, the second zeolite crystals are impregnated with a proton-generating species and the composition further includes third zeolite crystals comprising a water-retaining substance preferably selected from the group consisting of calcium chloride, magnesium sulfate, potassium chloride and potassium hydroxide. The composition can also include fourth zeolite crystals impregnated with at least one chloride dioxide-producing compound preferably selected from the group consisting of metal chlorites, metal chlorates, chloric acid and hypochlorous acid. Preferably, the composition is included in a container and the container can include a carbon dioxide-permeable barrier to allow the passage of carbon dioxide produced in the container, e.g., by exposing the contents of the container to a moisture-containing fluid. The permeable barrier can also be capable of controlling the release of carbon dioxide from the container.

In another alternative embodiment of the invention, the composition can include at least one carbon-containing compound selected from the group consisting of carbonates, bicarbonates or sesquicarbonates; at least one proton-generating species selected from the group consisting of aqueous acids and metal salts; and at least one water-retaining substance preferably selected from the group consisting of calcium chloride, magnesium sulfate, potassium chloride and potassium hydroxide. The carbon-containing compound can be in the form of a powder or a porous carrier such as zeolite crystals impregnated with the at least one carbon-containing compound. The zeolite crystals preferably include 1-50% of the at least one carbon-containing compound by weight, 0%-20% water by weight, and 50%-98.5% of the zeolite crystals by weight. The proton-generating species and the water-retaining substance are preferably in the form of zeolite crystals impregnated by the proton-generating species and the water-retaining substance. The composition can also include at least one chloride dioxide-producing compound preferably selected from the group consisting of metal chlorites, metal chlorates, chloric acid and hypochlorous acid. The composition is preferably provided in a container that can include a carbon dioxide-permeable barrier. The carbon-dioxide permeable barrier can also be capable of controlling the release of carbon dioxide from the container.

In yet another alternative embodiment of the invention, the composition can include zeolite crystals impregnated with at least one compound selected from the group consisting of a proton-generating species and a water-retaining substance and at least one carbon-containing compound selected from the group consisting of carbonates, bicarbonates or sesquicarbonates. The composition can include first zeolite crystals impregnated with a proton-generating species and second zeolite crystals impregnated with a water-retaining substance preferably selected from the group consisting of calcium chloride, magnesium sulfate, potassium chloride and potassium hydroxide. The composition can also include at least one chloride dioxide-producing compound preferably selected from the group consisting of metal chlorites, metal chlorates, chloric acid and hypochlorous acid, which can be in the form of zeolite crystals impregnated with the chloride dioxide-producing compound. The carbon-containing compound can be in the form of a powder and is preferably selected from the group consisting of sodium carbonate, sodium bicarbonate and sodium sesquicarbonate. The proton-generating species can be an aqueous acid or a metal salt. Preferably, the composition is included in a container and the container can include a carbon dioxide-permeable barrier to allow the passage of carbon dioxide produced in the container, e.g., by exposing the contents of the container to a moisture-containing fluid. The permeable barrier can also be capable of controlling the release of carbon dioxide from the container.

These and other features and advantages of the present invention will become more readily apparent to those skilled in the art upon consideration of the following detailed description, which describes both the preferred and alternative embodiments of the present invention.

DETAILED DESCRIPTION OF THE PREFERRED EMBODIMENTS

In the following detailed description, preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description. The term "comprising" and variations thereof as used herein is used synonymously with the term "including" and variations thereof and is an open, non-limiting term.

The present invention includes a method and composition for producing carbon dioxide that is based on carbon-containing compounds that react with protons to produce carbon dioxide. The carbon-containing compound is typically selected from the group consisting of carbonates, bicarbonates or sesquicarbonates and can be formed from cations selected from the group consisting of alkali metals, alkaline earth metals and ammonium. Preferably, the carbon-containing compound is sodium carbonate, sodium bicarbonate or sodium sesquicarbonate. More preferably, the carbon-containing compound is sodium carbonate, sodium bicarbonate, or a mixture thereof.

The carbon-containing compound can be provided in any form that allows it to react with protons to produce carbon dioxide. Preferably, the carbon-containing compound is in the form of a powder or a porous, preferably inert, carrier impregnated with the carbon-containing compound but can be an aqueous solution in some embodiments. The porous carrier has pores, channels or the like located therein and can be silica, pumice, diatomaceous earth, bentonite, or clay and is preferably zeolite crystals. The zeolite crystals can have a particle size (i.e., largest dimension) in the range from about 0.02 mm to about 1 inch (25 mm). For example, the zeolite crystals can have a particle size of about 0.125 inch, about 0.25 inch, about 0.50 inch, or about 0.75 inch, in their largest dimension, and can have dimensions substantially equal to 0.25 inch×0.167 inch, 0.125 inch×0.10 inch, 0.25 inch×0.125 inch, 0.125 inch×0.50 inch, or 0.50 inch×0.75 inch. The zeolite crystals are preferably uniformly impregnated throughout the volume of each crystal via the pores, channels, and the like, with the at least one carbon-containing compound.

The zeolite crystals are preferably impregnated with the carbon-containing compound by using zeolite crystals that have a moisture content at a low level, preferably less than or equal to about 5%. Zeolite crystals typically have an initial moisture content above this level and thus are dehydrated to produce the desired moisture content. The dehydrated zeolite crystals are then immersed in or sprayed with an aqueous solution of the carbon-containing compound at an elevated temperature (e.g., in the range from 120° F. to 190° F.) and the resulting slurry is thoroughly mixed. The mixed slurry is then air-dried to the desired moisture level, typically 0-20%, to produce the impregnated zeolite crystals of the invention. Alternatively, the impregnated zeolite crystals of the invention can be prepared without a drying step by calculating the amount of the aqueous solution of the carbon-containing compound needed to achieve the desired final moisture level (e.g., 15%) and adding this amount of the aqueous solution to the dehydrated zeolite crystals to impregnate the zeolite crystals. The zeolite crystals preferably include 1%50% carbon-containing compound, 0%-20% water, and 50%-98.5% zeolite by weight. In preferred embodiments, the zeolite crystals can include 1-25% carbon-containing compound, 4-8% water and 70%-94.5% zeolite by weight.

In addition to the carbon-containing compound, the compositions of the invention can include a water-retaining substance. The term "water-retaining substance" as used herein refers to deliquescents and other compounds that absorb or retain either liquid water or water vapor from air or other moisture-containing fluids. Suitable water-retaining substances include calcium chloride ($CaCl_2$), magnesium sulfate ($MgSO_4$), potassium chloride, and potassium hydroxide and preferably the water-retaining substance is calcium chloride. The water-retaining substance can be provided in any form that allows it to retain water and, like the carbon-containing compound, can be in the form of a powder or a porous carrier such as zeolite crystals impregnated with the water-retaining substance. The zeolite crystals impregnated with the carbon-containing compound can also be impregnated with the water-retaining substance through the use of an aqueous solution containing both the carbon-containing compound and the water-retaining substance. Alternatively, zeolite crystals separate from those that include the carbon-containing compound can be provided that are impregnated with the water-retaining substance and can be prepared in the manner described above. The water-retaining substance can be provided in an amount that controls the rate of release of carbon dioxide by controlling the rate at which protons are produced, e.g., by a proton-generating species as discussed below, and thus can control the rate at which carbon dioxide is produced. The rate at which the carbon dioxide is produced can, for example, be controlled by varying the relative amounts by weight of the carbon-containing compound and the water-retaining substance.

The composition can also include at least one chloride dioxide-producing compound. The chlorine dioxide-producing compound can be any compound that reacts with protons to produce chlorine dioxide and is preferably selected from the group consisting of metal chlorites, metal chlorates, chloric acid and hypochlorous acid. The metal chlorites and chlorates are typically in the form of alkali metal or alkaline earth metal chlorites and chlorates. The chlorine dioxide-producing compound is typically in the form of a powder or a porous carrier impregnated with the carbon-containing compound. The chlorine dioxide-producing compound is preferably impregnated in zeolite crystals as described above and as described in U.S. Pat. Nos. 5,567,405; 5,573,743; 5,730,948; 5,776,850; 5,853,689; 5,885,543; 6,174,508; 6,379,643; and 6,423,289, which are incorporated by reference herein in their entirety. The chlorine dioxide-producing compound produces chlorine dioxide by reacting with protons, in the same manner that the carbon-containing compound produces carbon dioxide. Systems that produce both carbon dioxide and chlorine dioxide are useful, e.g., for increasing the shelf life of food by killing both aerobic and anaerobic pathogens.

A proton-generating species preferably provides the protons of the invention. The proton-generating species can be provided in any form that allows the release of protons and can be in the form of a liquid, a powder or a porous carrier such as zeolite crystals impregnated with the proton-generating species. Typically, the zeolite crystals impregnated with the proton-generating species are separate from the zeolite crystals that are impregnated with the carbon-containing compound. The zeolite crystals are typically formed through the use of an aqueous solution of the proton-generating species in the manner described above with respect to the carbon-containing compound. The proton-generating species can be in the form of an aqueous acid or a metal salt. Typically, the metal salt is a chloride, sulfate, phosphate, propionate, acetate or citrate, that combines with water to produce an acid, i.e., protons. The metal is typically an alkali metal, alkaline earth metal or a transition metal. Suitable metal salts include ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate and sodium citrate. In addition to being a proton-generating species, the metal salt can in some cases also act as a water-retaining substance. For example, $CaCl_2$ and $MgSO_4$ are effective not only as water-retaining substances but also as generating protons.

The metal salts are activated to produce protons by contacting the metal salts with a moisture-containing (water-containing) fluid. Preferably, the metal salt is ferric chloride or ferric sulfate, or a mixture thereof, and these iron salts desirably absorb water in addition to functioning as a proton-generating species. More preferably, ferric chloride is used because it readily reacts with water to produce protons. The moisture-containing fluid can be liquid water or an aqueous solution or can be a moisture-containing gas such as air or water vapor. The protons produced by the proton-generating species react with the carbon-containing compound to produce carbon dioxide. The proton-generating species can also be activated other than by exposure to a moisture-containing fluid. For example, the proton-generating species can be activated and can release protons upon exposure to the water in the powders or impregnated zeolite crystals containing the carbon-containing compound.

As mentioned above, the proton-generating species can also be in the form of at least one acid. Suitable acids include acetic acid, citric acid, phosphoric acid, HCl, propionic acid, and sulfuric acid. Preferably, the acid is provided in the form of zeolite crystals impregnated with the acid and are produced by any suitable method. For example, U.S. Pat. Nos. 5,567,405 and 5,573,743 disclose methods for producing acid-impregnated zeolite crystals. The acid can also be in the form of a liquid (e.g. an aqueous acid solution) that can be applied to the carbon-containing compound, e.g., by spraying the carbon-containing compound in the form of a powder or an impregnated zeolite with the acid.

The present invention will now be described in further detail based on a preferred embodiment of the invention that uses sodium bicarbonate as the carbon-containing compound. As discussed above, other carbon-containing compounds can be used such as other bicarbonates, or carbonates or sesquicarbonates.

In one carbon dioxide-producing method in accordance with the invention, sodium bicarbonate powders are mixed with zeolite crystals impregnated with a proton-generating species: (1) phosphoric acid ($H_3PO_4$); (2) acetic acid ($CH_3COOH$); (3) citric acid; (4) ferric chloride ($FeCl_3$); (5) ferric sulfate; (6) another metal salt such as $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate and sodium citrate; (7) an acid other than phosphoric, acetic, or citric acid, or (8) another proton-generating species suitable for the particular application. Protons are slowly released from the zeolite crystals because of the presence of water in zeolite crystals and react with the sodium bicarbonate to produce carbon dioxide. Activation can be controlled by varying the ratio of sodium bicarbonate powders to zeolites impregnated with the proton-generating species, by including a water-retaining substance, by changing the particle size of the powder or zeolites, or by changing the chemical composition of the mixture.

In another carbon dioxide-producing method in accordance with the invention, a fluid, preferably a fluid such as air, water vapor, water, or an aqueous solution is allowed to contact a first bed of zeolite crystals impregnated with a proton-generating species: (1) phosphoric acid ($H_3PO_4$), (2) acetic acid ($CH_3COOH$), (3) citric acid, (4) ferric chloride ($FeCl_3$), (5) ferric sulfate, (6) another metal salt such as $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate and sodium citrate, (7) an acid other than phosphoric, acetic, or citric acid, or (8) another proton-generating species suitable for the particular application. Typically, the fluid is caused to move relative to the first bed of zeolite crystals. Then, the fluid is allowed to contact a second bed of sodium bicarbonate ($NaHCO_3$) powder, preferably, by causing the fluid to move relative to the second bed. Upon moving the fluid relative to the second bed, carbon dioxide is released due to contact with protons released by the acid or other proton-generating substance from the first bed. For example, it is believed that the carbon dioxide release occurs as a result of the following reaction, in the case of a first bed of zeolites impregnated with acetic acid and a second bed including sodium bicarbonate powder (where $Na(CH_3COO)$ is sodium acetate):

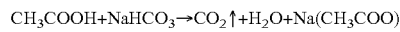

$$CH_3COOH + NaHCO_3 \rightarrow CO_2\uparrow + H_2O + Na(CH_3COO)$$

It is preferable for the fluid to flow through a first bed of proton-generating species-impregnated (e.g., acid-impregnated) zeolite crystals before the fluid flows through a second bed containing sodium bicarbonate powder. In particular, this sequence will result in protons entering the fluid due to interaction of the fluid with the acid or other proton-generating species in the crystals of the first bed. The presence of the protons (i.e., hydrogen ions) in the fluid will then enhance carbon dioxide production when the hydrogen ion-containing fluid interacts with the powder of the second bed.

While the foregoing process for producing carbon dioxide has been described with reference to two distinct (first and second) beds of impregnated zeolite crystals, a single bed containing a mixture of crystals can be used containing both impregnated zeolite crystals from the first bed described above and powders from the second bed described above. As an example, a mixed bed of carbon-containing powders mixed with zeolite crystals impregnated with phosphoric acid can be used to produce carbon dioxide by flowing a fluid through the mixed bed that activates the phosphoric acid to produce protons that react with the carbon-containing compound to produce carbon dioxide.

In an alternative embodiment of the invention, carbon dioxide can be produced by adding aqueous acid to a bed of zeolite crystals impregnated with a carbon-containing compound (e.g., sodium bicarbonate). The zeolite crystals impregnated with sodium bicarbonate can be immersed in or sprayed with aqueous acetic acid, phosphoric acid, citric acid, HCl, or sulfuric acid, with a concentration of 0.025% to 0.5% (i.e., the acid comprises 0.025% to 0.5% by weight of the combined impregnated zeolite and acid). Alternatively, another acid or other proton-generating species suitable for the particular application can be used to immerse or spray the impregnated zeolite crystals. Varying the amount and concentration of the added acid can also be used to control the rate of release of carbon dioxide.

In alternative embodiments, carbon dioxide is produced with a reversed sequence of distinct first and second beds, as follows. A fluid (e.g. water) is caused to move relative to a first bed. The first bed comprises zeolite crystals impregnated with sodium bicarbonate ($NaHCO_3$). Then, the fluid now containing sodium bicarbonate is caused to move relative to a second bed of zeolite crystals which are impregnated with a proton-generating species: (1) phosphoric acid, (2) acetic acid, (3)

citric acid, (4) ferric chloride ($FeCl_3$), (5) ferric sulfate, (6) another metal salt such as $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate and sodium citrate, (7) an acid other than phosphoric, acetic, or citric acid, or (8) another proton-generating species suitable for the particular application. Upon moving the fluid relative to the second bed, carbon dioxide is released.

In another embodiment of the invention, the method involves activating a mixture comprising carbon-containing powders or zeolite crystals impregnated with a carbon-containing compound, zeolite crystals impregnated with an acid or metal salt, and optionally also zeolite crystals impregnated with calcium chloride (or another water-retaining substance). The acid or metal salt reacts in the presence of water absorbed by the water-retaining substance to release protons, which in turn react with one or more of the other substances to produce carbon dioxide. Where sodium bicarbonate, ferric chloride, and sulfuric acid are present upon activation, e.g., the carbon dioxide-producing reaction is believed to be:

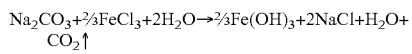

In this embodiment, the carbon-containing compound can be activated by simply mixing the components together. The activation can be further stimulated by exposing the mixture to a moisture-containing gas (e.g., air) or by causing water or a moisture-containing gas to flow through the mixture to achieve a higher carbon dioxide production rate.

In the embodiments discussed herein, the rate of carbon dioxide release upon activation of the zeolite crystal or powder mixture can be controlled in any of several ways, including appropriately selecting the concentration and amount of an activating acid or other proton-generating species, using impregnated zeolite crystals having an appropriately selected weight ratio of one or more of the impregnating substances (e.g., iron salt) to zeolite, adding a water-retaining substance (e.g., calcium chloride) to the mixture or into the carrier material and/or selecting an appropriate method for activating the mixture. For example, activation by exposing the mixture to moisture-containing gas typically results in a low carbon dioxide release rate, and activation by flowing water or moisture-containing gas through the mixture typically results in a higher carbon dioxide release rate. Prior to activation, the mixture of impregnated crystals should be as dry as possible. Preferably, the mixture is sealed within a dry, airtight capsule or other container and the container is unsealed or opened to expose the mixture to the activating fluid shortly before activation.

In another class of embodiments, the invention is a composition of matter that carries sufficient amounts of chemicals to be capable of releasing carbon dioxide to a target region upon activation by protons. The composition includes impregnated zeolite crystals including zeolite crystals impregnated with a carbon-containing compound, zeolite crystals impregnated with a proton-generating species, optionally zeolite crystals impregnated with a water-retaining substance, and optionally zeolite crystals impregnated with a chlorine dioxide-producing compound. Alternatively, a carbon-containing powder can be used in place of the zeolite crystals impregnated with a carbon-containing compound. Preferably, a carbon-containing powder with a water-retaining substance (e.g., calcium chloride) is used at a concentration which limits the rate of release of carbon dioxide to a predetermined maximum level to the target region in response to activation of carbon-containing powder with protons. For example, sodium bicarbonate powders can include, a water-retaining substance, and a zeolite impregnated with an acid or another proton-generating species. Such mixtures are activated by liquid water or atmospheric moisture to produce protons, which in turn react with the carbon-containing compound to produce carbon dioxide. The relative concentrations of impregnating chemicals will control the rate at which protons are produced and thus the rate at which carbon dioxide is produced in response to contact with water.

In some applications, it may be advantageous to separate the zeolite crystals from the target region through the use of a barrier such as a membrane. The barrier is preferably permeable to the flow of an activating fluid (e.g., air or water) from the target region such that the activating fluid will interact with the quantity of impregnated zeolite crystals in a manner resulting in production of protons, which in turn results in the production of carbon dioxide. The barrier is also preferably permeable to the flow of carbon dioxide to the target region. Preferably, the permeability of the barrier is such that it can control the release of carbon dioxide to the target region. For example, the permeability of the barrier can be such that the quantity of zeolite crystals is exposed to no more than a predetermined maximum flow rate of the activating fluid (e.g., the barrier is permeable to flow of the activating fluid from the target region at up to a predetermined maximum flow rate), so that the barrier limits to a predetermined maximum level the rate of proton generation and thus the rate of release of carbon dioxide to the target region. Alternatively, the permeability of the barrier can be such that it releases carbon dioxide at a predetermined maximum level and thus controls the rate of release of carbon dioxide to the target region. The barrier can also be used in conjunction with a container and containers for use in the invention are discussed above.

In accordance with the invention, carbon dioxide is produced by activating carbon-containing powders or impregnated crystals with protons, typically from a proton-generating source such as an acid impregnated zeolite or other such material. The materials can be mixed together and the generation of carbon dioxide is stimulated by particle-to-particle interactions. Carbon dioxide release can be further enhanced by environmental factors like moisture and temperature. Dry particle mixtures can be placed in fluids (e.g. air and other moisture-containing gases or water) and can be protected by appropriate packaging barriers or membranes to provide a substantially controlled release of carbon dioxide.

In some embodiments of the invention, the substances useful for producing carbon dioxide are stable in that they do not release carbon dioxide gas in significant amounts until activated by protons. One such embodiment includes one or more carbon containing-powders of sodium carbonate, sodium bicarbonate, or sodium sesquicarbonate, or mixtures thereof. Preferably, these powders have a small particle size in the range from 0.02 mm to one-quarter inch (6.3 mm).

Another such embodiment includes one or more zeolite crystals impregnated with sodium carbonate, bicarbonate, or sesquicarbonate, and mixtures thereof. Preferably, the zeolite crystals are small and have a particle size in a range from 0.02 mm to one-quarter inch. The crystals also preferably include 1%-50% (1-25% in some preferred embodiments) sodium carbonate, bicarbonate, or sesquicarbonate or mixtures thereof, 0%-20% (4%-8% in some preferred embodiments) water, and 50%-98.5% (70%-94.5% in some preferred embodiments) zeolite by weight.

In any of the embodiments discussed herein, a water-retaining substance such as calcium chloride, magnesium sulfate, potassium chloride, or potassium hydroxide can be included in the invention and, preferably, the water retaining-substance is calcium chloride. The inventors have found that the presence of a sufficient amount of a water-retaining substance in the composition of the invention reduces the rate of carbon dioxide outgassing in impregnated zeolites to no more than a negligible amount at times prior to activation of the composition with protons and yet allows release of carbon dioxide at a desired rate following activation of the composition with protons. It is believed that one of the reasons for carbon dioxide outgassing prior to activation with protons from zeolite impregnated with the at least one carbon-containing compound but not impregnated with a water-retaining substance is the migration of protons in the aluminosilicates comprising the zeolite.

In yet another embodiment of the invention, the method for producing carbon dioxide includes a zeolite crystal mixture, wherein the mixture comprises carbon-containing powders or zeolite crystals impregnated with at least one carbon-containing compound and zeolite crystals impregnated with at least one chloride dioxide-producing compound preferably selected from the group consisting of metal chlorites, metal chlorates, chloric acid and hypochlorous acid. The mixture can be activated with protons to produce both carbon dioxide and chlorine dioxide.

In other embodiment of the invention, the method for producing carbon dioxide includes providing a zeolite crystal mixture wherein the mixture comprises zeolite crystals impregnated with a proton-generating species. The zeolite crystal mixture is contacted with a solution including the at least one carbon-containing compound to generate protons and thus to produce carbon dioxide. The invention will now be further described by the following non-limiting examples.

Example 1

Two grams of sodium carbonate were mixed with 14 grams of 25 wt % ferric chloride impregnated zeolite and exposed to 100% relative humidity over 116 hours. Carbon dioxide was recovered in the amount provided below:

| Time, Hours | Cumulative $CO_2$ Liters/gm $Na_2CO_2$ |
|---|---|
| 1 | 0.02 |
| 3 | 0.04 |
| 22 | 0.12 |
| 49 | 0.17 |
| 116 | 0.20 |

Example 2

Two grams of sodium bicarbonate were mixed with 60 grams of 25 wt % ferric chloride impregnated zeolite and exposed to 100% relative humidity over 71 hours. Carbon dioxide was recovered in the amount provided below:

| Time, Hours | Cumulative $CO_2$ Liters/gm $NaHCO_2$ |
|---|---|
| 0.25 | 0.10 |
| 0.75 | 0.16 |
| 1.75 | 0.22 |
| 70.5 | 0.29 |

Example 3

Ten grams of 20% wt $Na_2CO_3$ impregnated zeolite were mixed with 14 grams of 25 wt % ferric chloride impregnated zeolite and exposed to 100% relative humidity over 77 hours. Carbon dioxide was recovered in the amount provided below:

| Time, Hours | Cumulative $CO_2$ Liters/gm $Na_2CO_3$ |
|---|---|
| 0.25 | 0.01 |
| 1.75 | 0.03 |
| 5.7 | 0.07 |
| 77 | 0.16 |

It is understood that upon reading the above description of the present invention and reviewing, one skilled in the art could make changes and variations therefrom. These changes and variations are included in the spirit and scope of the following appended claims.

That which is claimed:

1. A composition of matter for the production of carbon dioxide, comprising:
   (a) at least one carbon-containing compound selected from the group consisting of carbonates, bicarbonates, sesquicarbonates, and mixtures thereof;
   (b) a porous carrier selected from the group consisting of zeolite crystals, silica, pumice, diatomaceous earth, bentonite, and clay impregnated with at least one species selected from the group consisting of aqueous acids, metal salts and mixtures thereof; and
   (c) at least one water-retaining substance selected from the group consisting of calcium chloride, magnesium sulfate, potassium chloride, potassium hydroxide, and mixtures thereof.

2. The composition according to claim 1, wherein said at least one water-retaining substance is impregnated in a porous carrier.

3. The composition according to claim 1, further comprising at least one chlorine dioxide-producing compound selected from the group consisting of metal chlorites, metal chlorates, chloric acid, and hypochlorous acid.

4. The composition according to claim 3, wherein said at least one chlorine dioxide-producing compound is impregnated in a porous carrier.

5. The composition according to claim 1, wherein said species comprises an aqueous solution.

6. The composition according to claim 1, wherein said species comprises at least one metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, and sodium citrate.

7. The composition according to claim 1, wherein said species comprises a mineral acid selected from the group consisting of hydrochloric acid, phosphoric acid, and sulfuric acid.

8. The composition according to claim 1, wherein said at least one carbon-containing compound is impregnated in a porous carrier.

9. The composition according to claim 1, wherein said at least one carbon-containing compound is in powdered form.

10. A composition of matter for the production of carbon dioxide comprising:
   (a) at least one carbon-containing compound selected from the group consisting of carbonates, bicarbonates, sesquicarbonates, and mixtures thereof impregnated in a first porous carrier selected from the group consisting of zeolite crystals, silica, pumice, diatomaceous earth, bentonite, and clay; and (b) a species selected from the group consisting of aqueous acids, metal salts, and mixtures thereof impregnated in a separate, second porous carrier selected from the group consisting of zeolite crystals, silica, pumice, diatomaceous earth, bentonite, and clay.

11. The composition according to claim 10, wherein the at least one carbon-containing compound is selected from the group consisting of sodium carbonate, sodium bicarbonate, and sodium sesquicarbonate.

12. The composition according to claim 10, further comprising at least one water-retaining substance.

13. The composition according to claim 12, wherein said at least one water-retaining substance is impregnated in a third porous carrier.

14. The composition according to claim 10, further comprising at least one chlorine dioxide-producing compound.

15. The composition according to claim 14, wherein said at least one chlorine dioxide-producing compound is impregnated in a fourth porous carrier.

16. The composition according to claim 10, wherein said second porous carrier includes zeolite crystals.

17. The composition according to claim 16, wherein at least a portion of said first porous carrier comprises 1%-50% by weight of the at least one carbon-containing compound, 0-20% by weight water, and 50%-98.5% by weight of said zeolite crystals.

18. The composition according to claim 10, wherein said metal salt includes at least one metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate and sodium citrate.

19. The composition according to claim 10, wherein said acid includes a mineral acid selected from the group consisting of hydrochloric acid, phosphoric acid, and sulfuric acid.

20. A method for producing carbon dioxide, comprising:
    (a) providing at least one carbon-containing compound selected from the group consisting of carbonates, bicarbonates sesquicarbonates, and mixtures thereof impregnated in a first porous carrier selected from the group consisting of zeolite crystals, silica, pumice, diatomaceous earth, bentonite, and clay;
    (b) providing a species selected from the group consisting of aqueous acids, metal salts, and mixtures thereof impregnated in a separate, second porous carrier selected from the group consisting of zeolite crystals, silica, pumice, diatomaceous earth, bentonite, and clay;
    (c) activating the species to produce protons from water present in or introduced to the second porous carrier; and
    (d) reacting the protons and the at least one carbon-containing compound to produce carbon dioxide.

21. The method according to claim 20, further comprising the step of providing a water-retaining substance selected from the group consisting of calcium chloride, magnesium sulfate, potassium chloride, and potassium hydroxide.

22. The method according to claim 21, wherein the water-retaining substance is impregnated in a porous carrier.

23. The method according to claim 20, further comprising the step of providing a third porous carrier impregnated with at least one chlorine dioxide-producing compound selected from the group consisting of metal chlorites, metal chlorates, chloric acid, and hypochlorous acid, and wherein said reacting step further comprises reacting protons with the at least one chlorine-dioxide producing compound to produce chlorine dioxide.

24. The method according to claim 20, wherein the second porous carrier is impregnated with a metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, and sodium citrate, and wherein said activating step comprises contacting the metal salt with water.

25. The method according to claim 20, wherein the at least one carbon-containing compound is selected from the group consisting of sodium carbonate, sodium bicarbonate, and sodium sesquicarbonate.

26. The method according to claim 20, further comprising the step of controlling the release of the carbon dioxide produced in step (d) through using a permeable barrier.

27. A method for producing carbon dioxide, including the steps of:
    (a) providing at least one carbon-containing compound selected from the group consisting of carbonates, bicarbonates, sesquicarbonates, and mixtures thereof;
    (b) providing a porous carrier selected from the group consisting of zeolite crystals, silica, pumice, diatomaceous earth, bentonite, and clay impregnated with a species selected from the group consisting of aqueous acids, metal salts, and mixtures thereof;
    (c) providing a water-retaining substance selected from the group consisting of calcium chloride, magnesium sulfate, potassium chloride, potassium hydroxide, and mixtures thereof;
    (d) activating the species to produce protons from water present in or introduced to the porous carrier; and
    (e) reacting the protons and the at least one carbon-containing compound to produce carbon dioxide.

28. The method according to claim 27, further comprising the step of providing at least one chlorine dioxide-producing compound selected from the group consisting of metal chlorites, metal chlorates, chloric acid, and hypochlorous acid, and wherein said reacting step further comprises reacting protons with the at least one chlorine-dioxide producing compound to produce chlorine dioxide.

29. The method according to claim 27, wherein said at least one carbon-containing compound is in powdered form.

30. A method for producing carbon dioxide, comprising:
    (a) providing at least one carbon-containing compound selected from the group consisting of carbonates, bicarbonates, sesquicarbonates, and mixtures thereof;
    (b) providing a species comprising a metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, and sodium citrate, and mixtures thereof;
    (c) providing a porous carrier selected from the group consisting of zeolite crystals, silica, pumice, diatomaceous earth, bentonite, and clay impregnated with at least one water-retaining substance selected from the group consisting of calcium chloride, magnesium sulfate, potassium chloride, potassium hydroxide, and mixtures thereof;
    (d) activating the species to produce protons from water present in or introduced to the porous carrier; and
    (e) reacting the protons and the at least one carbon-containing compound to produce carbon dioxide.

31. The method according to claim 30, wherein said activating step comprises contacting said species with water.

32. The method according to claim 30, wherein at least one of said at least one carbon-containing compound and said species are impregnated in porous carriers selected from the group consisting of zeolite crystals, silica, pumice, diatomaceous earth, bentonite, and clay.

33. The method according to claim 30, wherein said species comprises a mineral acid selected from the group consisting of hydrochloric acid, phosphoric acid, and sulfuric acid.

34. The method according to claim 31, wherein said species is impregnated on a porous carrier, and wherein said water comprises moisture inherently contained within at least one of said at least one carbon-containing compound and said porous carrier.

35. A method for producing carbon dioxide, comprising:
(a) providing at least one carbon-containing compound selected from the group consisting of carbonates, bicarbonates, sesquicarbonates, and mixtures thereof;
(b) providing a porous carrier selected from the group consisting of zeolite crystals, silica, pumice, diatomaceous earth, bentonite, and clay impregnated with an aqueous solution comprising a species selected from the group consisting of aqueous acids, metal salts, and mixtures thereof;
(c) providing a water-retaining substance selected from the group consisting of calcium chloride, magnesium sulfate, potassium chloride, potassium hydroxide, and mixtures thereof;
(d) generating protons as a result of the reaction of said species and the water present in said aqueous solution;
(e) contacting the aqueous solution comprising said protons with said at least one carbon-containing compound; and
(f) reacting the protons with said at least one carbon-containing compound to produce carbon dioxide.

36. The method according to claim 27, wherein the release of said carbon dioxide is substantially controlled by the weight ratios of said at least one carbon-containing compound, said porous carrier, and said water-retaining substance.

37. The method according to claim 36, wherein the release of said carbon dioxide is substantially controlled by the weight ratio of said species to said porous carrier.

38. The method according to claim 36, wherein the release of said carbon dioxide is substantially controlled by the weight ratio of said species to said at least carbon-containing compound.

39. The method according to claim 36, wherein the release of said carbon dioxide is substantially controlled by the weight ratio of said water-retaining substance to said species or said at least one carbon-containing compound.

40. A composition of matter for the production of carbon dioxide, comprising:
(a) at least one carbon-containing compound selected from the group consisting of carbonates, bicarbonates, sesquicarbonates, and mixtures thereof;
(b) at least one species comprising a metal salt selected from the group consisting of ferric chloride, ferric sulfate, $CaCl_2$, $ZnSO_4$, $ZnCl_2$, $CoSO_4$, $CoCl_2$, $MnSO_4$, $MnCl_2$, $CuSO_4$, $CuCl_2$, $MgSO_4$, sodium acetate, sodium citrate, and mixtures thereof; and
(c) at least one water-retaining substance selected from the group consisting of calcium chloride, magnesium sulfate, potassium chloride, potassium hydroxide, and mixtures thereof impregnated in a porous carrier selected from the group consisting of zeolite crystals, silica, pumice, diatomaceous earth, bentonite, and clay.

41. The composition according to claim 40, wherein said at least one carbon-containing compound is in powdered form.

42. The composition according to claim 40, further comprising at least one chlorine dioxide-producing compound selected from the group consisting of metal chlorites, metal chlorates, chloric acid, and hypochlorous acid.

43. The composition according to claim 1, wherein the at least one carbon-containing compound is also impregnated in the porous carrier.

44. The composition according to claim 27, wherein the at least one carbon-containing compound is also impregnated in the porous carrier.

* * * * *

UNITED STATES PATENT AND TRADEMARK OFFICE
CERTIFICATE OF CORRECTION

PATENT NO. : 7,922,992 B2 Page 1 of 1
APPLICATION NO. : 10/243590
DATED : April 12, 2011
INVENTOR(S) : Ernst et al.

It is certified that error appears in the above-identified patent and that said Letters Patent is hereby corrected as shown below:

Column 14,
Line 34, "chioric acid" should read --chloric acid--.

Signed and Sealed this
Fifteenth Day of May, 2012

David J. Kappos
*Director of the United States Patent and Trademark Office*